(12) United States Patent
Shippert

(10) Patent No.: US 8,887,770 B1
(45) Date of Patent: Nov. 18, 2014

(54) VESSEL FILL CONTROL METHOD AND APPARATUS

(76) Inventor: Ronald D. Shippert, Littleton, CO (US)

( * ) Notice: Subject to any disclaimer, the term of this patent is extended or adjusted under 35 U.S.C. 154(b) by 754 days.

(21) Appl. No.: 13/050,749

(22) Filed: Mar. 17, 2011

(51) Int. Cl.
*B65B 31/04* (2006.01)
*A61M 1/00* (2006.01)

(52) U.S. Cl.
USPC ............. 141/65; 141/234; 141/236; 141/340; 604/319

(58) Field of Classification Search
CPC ........................ A61M 1/0001; A61M 1/0003
USPC ...................... 141/65, 234–247; 604/317–326
See application file for complete search history.

(56) References Cited

U.S. PATENT DOCUMENTS

| | | | |
|---|---|---|---|
| 1,138,764 A | 5/1915 | Kline | |
| 3,223,490 A * | 12/1965 | Sacken et al. | 422/219 |
| 3,434,869 A | 3/1969 | Davidson | |
| 3,664,387 A * | 5/1972 | Cates, Jr. | 141/238 |
| 3,693,673 A * | 9/1972 | Oates | 141/237 |
| 3,993,080 A | 11/1976 | Loseff | |
| 4,359,049 A | 11/1982 | Redl et al. | |
| 4,447,230 A | 5/1984 | Gula et al. | |
| 4,492,258 A * | 1/1985 | Lichtenstein et al. | 141/1 |
| 4,548,207 A | 10/1985 | Reimels | |
| 4,683,884 A | 8/1987 | Hatfield et al. | |
| 4,753,634 A | 6/1988 | Johnson | |
| 4,770,187 A | 9/1988 | Lash et al. | |
| D298,650 S | 11/1988 | Lash | |
| 4,834,703 A | 5/1989 | Dubrul et al. | |
| 4,883,755 A | 11/1989 | Carabasi et al. | |
| 4,957,492 A | 9/1990 | McVay | |
| 5,035,708 A | 7/1991 | Alchas | |
| 5,049,146 A | 9/1991 | Bringham et al. | |
| 5,052,999 A | 10/1991 | Klein | |
| 5,158,533 A * | 10/1992 | Strauss et al. | 604/6.09 |
| 5,312,380 A | 5/1994 | Alchas et al. | |
| 5,338,294 A | 8/1994 | Blake, III | |
| 5,352,194 A | 10/1994 | Greco et al. | |
| 5,352,410 A | 10/1994 | Hansen et al. | |
| 5,372,945 A | 12/1994 | Alchas et al. | |
| 5,441,539 A | 8/1995 | Alchas et al. | |
| 5,569,178 A | 10/1996 | Henley | |
| 5,603,845 A | 2/1997 | Holm | |
| 5,766,134 A | 6/1998 | Lisak et al. | |

(Continued)

FOREIGN PATENT DOCUMENTS

| | | |
|---|---|---|
| EP | 1531881 | 5/2005 |
| EP | 1531882 | 5/2005 |

(Continued)

OTHER PUBLICATIONS

LipiVage, product insert, 2 pages, Aug. 2004.

(Continued)

*Primary Examiner* — Timothy L Maust
(74) *Attorney, Agent, or Firm* — Sheridan Ross P.C.

(57) ABSTRACT

Methods and systems for filling a container with material to a desired level are provided. In particular, a container to be filled is associated with a funnel. The funnel occupies a selected or reserved amount of the container volume. Moreover, the volume of the funnel is less than the reserved volume of the container. Accordingly, by filling the container and the attached funnel to the top of the funnel, and then removing the funnel, the container is filled to less than a maximum level.

16 Claims, 14 Drawing Sheets

(56) References Cited

U.S. PATENT DOCUMENTS

| | | | |
|---|---|---|---|
| 5,786,207 A | 7/1998 | Katz et al. | |
| 5,804,366 A | 9/1998 | Hu et al. | |
| 5,827,217 A | 10/1998 | Silver et al. | |
| 5,911,700 A | 6/1999 | Mozsary et al. | |
| 5,976,470 A | 11/1999 | Maiefski et al. | |
| 6,013,048 A | 1/2000 | Podany et al. | |
| 6,024,725 A | 2/2000 | Bollinger et al. | |
| 6,258,054 B1 | 7/2001 | Mozsary et al. | |
| 6,299,763 B1 | 10/2001 | Ashman | |
| 6,303,286 B1 | 10/2001 | Dennis et al. | |
| 6,315,756 B1 | 11/2001 | Tankovich | |
| 6,316,247 B1 | 11/2001 | Katz et al. | |
| 6,468,225 B1 | 10/2002 | Lundgren | |
| 6,494,876 B1 | 12/2002 | Fowler et al. | |
| 6,623,733 B1 | 9/2003 | Hossainy et al. | |
| 6,626,890 B2 | 9/2003 | Nguyen et al. | |
| 6,777,234 B1 | 8/2004 | Dennis et al. | |
| 6,905,660 B2 * | 6/2005 | Harper et al. | 422/232 |
| 6,991,765 B2 * | 1/2006 | Neilson et al. | 422/553 |
| 7,097,690 B2 | 8/2006 | Usher et al. | |
| 7,121,309 B2 * | 10/2006 | Goemans et al. | 141/237 |
| 7,335,513 B2 | 2/2008 | Smith | |
| 7,390,484 B2 | 6/2008 | Fraser et al. | |
| 7,687,059 B2 | 3/2010 | Fraser et al. | |
| 8,622,997 B2 | 1/2014 | Shippert | |
| 2002/0146817 A1 | 10/2002 | Cannon et al. | |
| 2002/0198474 A1 | 12/2002 | Becker | |
| 2003/0161816 A1 | 8/2003 | Fraser et al. | |
| 2003/0162707 A1 | 8/2003 | Fraser et al. | |
| 2004/0067219 A1 | 4/2004 | Vida | |
| 2004/0097867 A1 | 5/2004 | Fraser et al. | |
| 2004/0106196 A1 | 6/2004 | Fraser et al. | |
| 2005/0025755 A1 | 2/2005 | Hendrick | |
| 2005/0084961 A1 | 4/2005 | Hendrick et al. | |
| 2005/0186671 A1 | 8/2005 | Cannon et al. | |
| 2006/0093527 A1 | 5/2006 | Buss | |
| 2006/0213374 A1 | 9/2006 | Shippert | |
| 2006/0258004 A1 | 11/2006 | Kosnik et al. | |
| 2007/0100277 A1 | 5/2007 | Shippert | |
| 2007/0225686 A1 | 9/2007 | Shippert | |
| 2008/0014181 A1 | 1/2008 | Ariff et al. | |
| 2008/0058763 A1 | 3/2008 | Boland et al. | |
| 2008/0154240 A1 | 6/2008 | Shippert | |
| 2009/0192454 A1 | 7/2009 | Boland et al. | |
| 2010/0280496 A1 | 11/2010 | Shippert | |
| 2014/0130936 A1 | 5/2014 | Shippert | |

FOREIGN PATENT DOCUMENTS

| | | |
|---|---|---|
| EP | 1921133 | 5/2008 |
| WO | WO 00/77164 | 12/2000 |
| WO | WO 2004/067065 | 8/2004 |
| WO | WO 2005/011569 | 2/2005 |
| WO | WO 2005/012480 | 2/2005 |
| WO | WO 2005/034843 | 4/2005 |
| WO | WO 2005/095581 | 10/2005 |
| WO | WO 2006/014156 | 2/2006 |
| WO | WO 2006/014159 | 2/2006 |
| WO | WO 2006/022612 | 3/2006 |
| WO | WO 2006/026969 | 3/2006 |
| WO | WO 2006/127007 | 11/2006 |
| WO | WO 2008/137234 | 11/2008 |
| WO | WO 2009/149691 | 12/2009 |

OTHER PUBLICATIONS

Genesis Biosystems, Advancing the Science of Skincare, LipiVage, 1 page, at http://www.dermagenesis.com/prodlipivage.cfm, printed Oct. 25, 2004.

Genesis Biosystems, Advancing the Science of Skincare, LipiVage, 3 pages, at http://www.dermagenesis.com/prodlipivage.cfm, printed Mar. 16, 2005.

LipiVage Fat Harvest, Wash & Transfer System, available at www.lipivage.com, Genesis Biosystems, Inc., 2 pages, printed Sep. 21, 2005.

Lee W. Young, Written Opinion for International (PCT) Patent Application No. PCT/US08/59469, mailed Aug. 28, 2008, pp. 1-5.

Lee W. Young, International Search Report for International (PCT) Patent Application No. PCT/US 08/59469, mailed Aug. 28, 2008, pp. 1-3.

Restriction Requirement for U.S. Appl. No. 11/088,598, filed Mar. 23, 2005, mailed Feb. 12, 2009, pp. 1-5.

Office Action for U.S. Appl. No. 11/088,598, mailed Jul. 21, 2009, pp. 1-15.

Final Office Action for U.S. Appl. No. 11/088,598, mailed Mar. 3, 2010, pp. 1-17.

Interview Summary for U.S. Appl. No. 11/088,598, mailed May 19, 2010, 3 pages.

Notice of Allowance and Fee(s) Due for U.S. Appl. No. 11/088,598, mailed Jun. 10, 2010, 8 pages.

Restriction Requirement for U.S. Appl. No. 11/553,920, filed Oct. 27, 2006, mailed Feb. 12, 2009, pp. 1-5.

Office Action for U.S. Appl. No. 11/553,921, mailed Jul. 7, 2009, pp. 1-11.

Final Office Action for U.S. Appl. No. 11/553,920, mailed Mar. 26, 2010, pp. 1-11.

Interview Summary for U.S. Appl. No. 11/553,920, mailed May 19, 2010, 4 pages.

Notice of Allowance and Fee(s) Due for U.S. Appl. No. 11/553,920, mailed Jun. 10, 2010, 8 pages.

Restriction Requirement for U.S. Appl. No. 11/742,452, filed Apr. 30, 2007, mailed Feb. 20, 2009, pp. 1-5.

Office Action for U.S. Appl. No. 11/742,452, filed Apr. 30, 2007, mailed May 12, 2009, pp. 1-7.

Final Office Action for U.S. Appl. No. 11/742,452, mailed Nov. 6, 2009, 10 pages.

Interview Summary for U.S. Appl. No. 11/742,452, mailed Dec. 16, 2009, pp. 1-3.

Office Action for U.S. Appl. No. 11/742,452, mailed Jan. 4, 2010, 4 pages.

Restriction Requirement for U.S. Appl. No. 12/046,300, mailed Aug. 30, 2010, 6 pages.

Official Action for U.S. Appl. No. 12/046,300, mailed Oct. 13, 2010, 33 pages.

Official Action for U.S. Appl. No. 12/046,300, mailed Mar. 22, 2011, 7 pages.

Notice of Allowance and Fee(s) Due for U.S. Appl. No. 12/046,300, mailed Sep. 20, 2011, 6 pages.

Restriction Requirement for U.S. Appl. No. 12/484,781, mailed Jul. 7, 2011, 6 pages.

Official Action for U.S. Appl. No. 12/484,781, mailed Oct. 5, 2011, 30 pages.

"Innovative Time-Saving Products, vol. VII," Shippert Medical Technologies Incorporated, Apr. 2010, 40 pages.

Official Action for U.S. Appl. No. 13/174,169, mailed Jun. 5, 2014, 7 pages.

Final Official Action for U.S. Appl. No. 12/484,781, mailed Apr. 23, 2012, 12 pages.

Notice of Allowance for U.S. Appl. No. 12/484,781, mailed Sep. 18, 2013, 8 pages.

Notice of Allowance and Fee(s) Due for U.S. Appl. No. 11/742,452, mailed Jan. 4, 2010, 4 pages.

Notice of Allowability for U.S. Appl. No. 11/742,452, mailed May 19, 2010, 9 pages.

Advisory Action for U.S. Appl. No. 12/484,781, mailed Jul. 9, 2012, 3 pages.

* cited by examiner

VESSEL FILL CONTROL METHOD AND APPARATUS

FIELD

The present invention is directed to methods and apparatuses for filling containers. More particularly, methods and apparatuses are provided for filling containers to a desired fill level.

BACKGROUND

In various applications, it is desirable to fill containers or vessels with fluids or other material. In doing so, it is often desirable to control the level to which a container is filled with the material. For example, it can be desirable to fill a container to a level somewhere below a maximum, in order to leave head space and/or to allow for or to facilitate the addition of a closure or seal to the container.

In the context of a production or manufacturing facility, mechanisms can be provided for filling containers with a fixed volume or amount of material. Such mechanisms can determine fill levels using sensors that detect the amount of material by weight, or by the level to which the container has been filled with the material. Still other mechanisms can make use of valves that introduce material at a known pressure for a known period of time. Although such mechanisms have wide application, their cost and complexity make them ill-suited to applications where the volume of material and/or number of containers being filled is comparatively limited.

One exemplary context in which it is desirable to fill containers with material to a level less than a maximum fill level is in the field of micro-lipoinjection. Micro-lipoinjection is a process in which fat is taken from one spot in the body and re-injected in another place in the body. It is desirable to limit the amount of handling undergone by the fat after it has been removed, but prior to re-injection in the body. Accordingly, it is desirable to place fat removed from a body in a syringe, so that the fat is ready for re-injection into the body. In order to facilitate the insertion of a plunger into the barrel of the syringe, it is preferable that the syringe barrel not be completely filled with fat. However, controlling the fill level of the syringe barrel is a task that typically requires the attention of personnel while the fat transfer procedure is being performed.

SUMMARY

Embodiments of the present invention are directed to solving these and other problems and disadvantages of the prior art. In accordance with embodiments of the present invention, an apparatus is provided for filling a container to a level that is less than a maximum level in a controlled, automatic manner. In particular, once a vessel or container has been filled with material, additional material is deposited in a further container or is discarded. Accordingly, one or more containers can be filled to a desired level without requiring active control and/or constant attention by an operator.

In accordance with at least some embodiments of the present invention, a funnel having a securement section and a reduced section is provided. The funnel fits into the open end of a container to be filled. More particularly, the reduced section of the funnel extends some distance into the container, while the securement section forms an interconnection with the interior of the container by friction. Material, such as but not limited to a fluid, can then be poured into the container, filling at least a portion of the container's volume, and also filling at least a portion of the funnel's volume. The funnel can then be removed, leaving the container partially filled. In particular, the dimensions of the funnel, including the extent to which the funnel occupies a portion of the container volume, are selected to create a reserved volume to leave an unfilled or head space volume after the funnel has been removed from the container and the material held by the funnel has fallen or dropped into the container. Therefore, in accordance with embodiments of the present invention, the reserved volume is less than the volume defined by the funnel. Thus, when the funnel is removed from the container, the material that was held in the funnel partially fills the reserved volume, leaving the container partially filled. A system in accordance with embodiments of the present invention may include multiple containers that are each associated with a funnel. Accordingly, multiple containers can be filled.

In accordance with other embodiments of the present invention, a funnel is provided that, when the apparatus is assembled, does not contact an interior surface of the associated container. In particular, although the funnel extends into the interior volume of the container, the funnel does not contact the interior diameter or surface of the container. With respect to such embodiments, the container may be held by a tray that allows access to the open top of the container. The tray can be held by a support member. As an example, the support member can include an outer container. The funnel can be formed as part of a manifold assembly that allows the funnel to at least partially extend into the container, without touching the inside surface of the container. The container can include a perforated container. In embodiments having a perforated container, that container can be disposed within an outer container. In addition, a waste tube with a first or inlet end on a floor of the outer container and a second end connected to a vacuum source can be included. Moreover, multiple containers, each associated with a funnel can be included.

Where multiple funnels are provided for filling multiple containers, the funnels may be associated with a common manifold assembly. The manifold assembly can include a material transfer channel with a first or inlet end, comprising or adjacent an inlet that receives material for placement in the containers. A second end of the material transfer channel may comprise or be associated with an outlet, through which a vacuum is applied to the inlet, for moving material. Multiple funnels may be placed at intervals along the material transfer channel. In such embodiments, material, such as a fluid, received at the inlet, will collect in a first container fed by a first funnel placed along the tissue transfer channel. When the first funnel and container assembly has been filled to the top of the funnel interconnected to the container, additional material will be carried to the second funnel and container assembly by the material transfer channel, and accumulate in the second container, and so on. Accordingly, multiple containers can be filled in series. Multiple funnel embodiments can include funnels with securement sections that interconnect to the containers. Alternatively, multiple funnel embodiments can be associated with a tray having a plurality of apertures for receiving a plurality of containers, with the funnels being associated with a lid assembly, such that, when assembled, each container is associated with a funnel that occupies at least a portion of the container volume. Moreover, the multiple containers can be impermeable, or can be perforated.

Methods in accordance with embodiments of the present invention include partially filling a container with a material by establishing a reserved volume in a container. More particularly, establishing a reserved volume can be performed using a funnel that has a securement section and a reduced section. Alternatively, a reserved volume can be established using a funnel that is provided as part of a tray that locates the funnel relative to the container, and that allows the funnel to occupy a portion of the volume defined by the container, but without contacting the interior surface of the container. In accordance with still other embodiments, a reserved volume can be established using a solid funnel or spacer that itself provides zero volume for material and that occupies a portion of the volume defined by the container. The reserved volume created by the funnel, in the form of a portion of the container volume being occupied by the funnel, and the selection of a funnel volume that is less than the reserved volume, results in the creation of a head space between the top of the container and a level at or near the bottom of the funnel. According to at least some embodiments of the method, the container and funnel are filled, with the funnel in place such that it occupies a portion of the container volume, to at or near the top of the funnel. The container and the funnel can then be disconnected from one another, while allowing the material held in the funnel to drop into the container. The container will then have a volume of material that fills the container to a level that is less than a maximum capacity of the container.

Additional features and advantages of embodiments of the present invention will become more readily apparent from the following discussion, particularly when taken together with the accompanying drawings.

DETAILED DESCRIPTION

Figure 1:
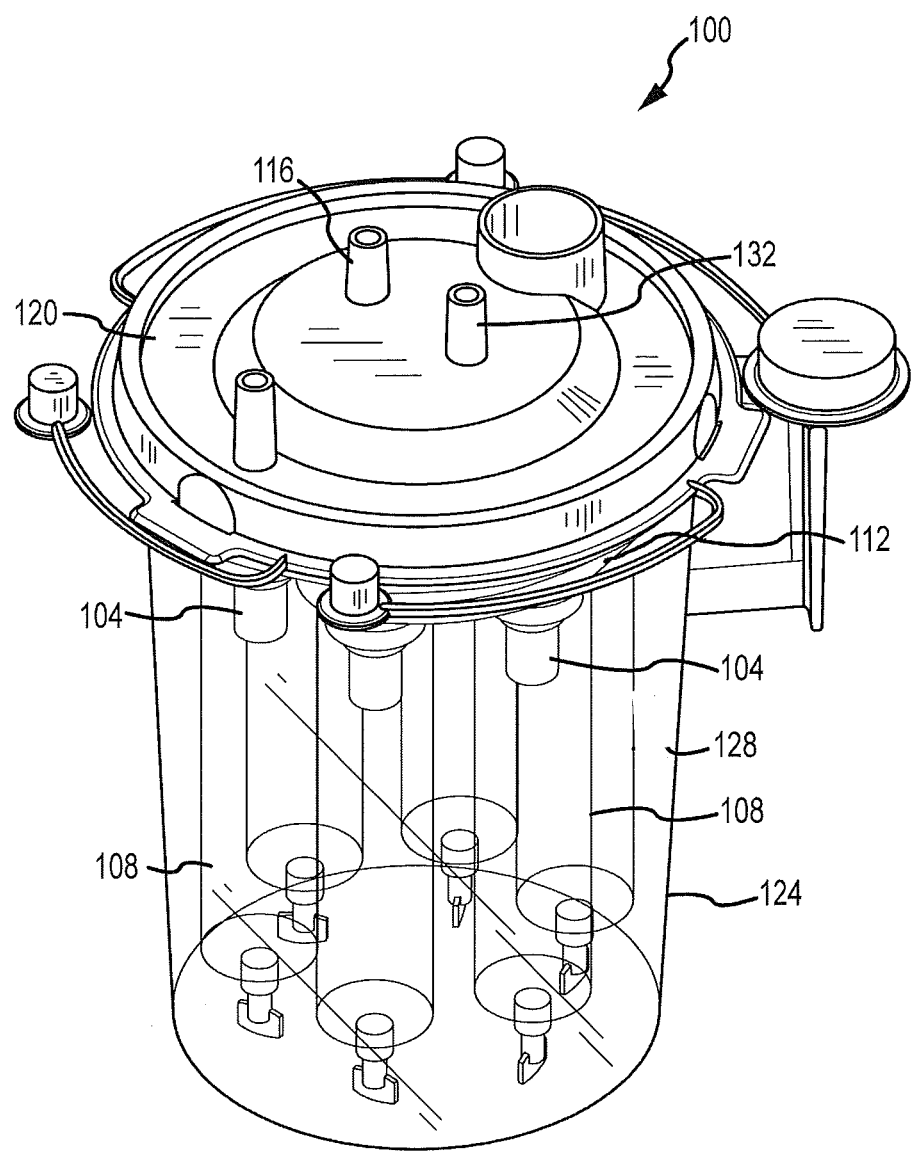
FIG. 1 is a top perspective view of a system for filling containers in accordance with embodiments of the present invention.

FIG. 1 is a perspective view of a system 100 for filling containers in accordance with embodiments of the present invention. In general, the system includes one or more funnels 104 and one or more containers 108. In the illustrated embodiment, the funnels 104 are associated with a manifold assembly 112. The manifold assembly 112 receives material to be loaded into the containers 108 through an inlet 116 formed in a lid 120. The lid 120, together with an outer container 124, define an enclosed volume 128 in which the containers 108 are held. In accordance with embodiments of the present invention, the enclosed volume 128 may comprise a sterilized volume. Therefore, by maintaining the containers 108 within the enclosed volume 128 until they are filled and ready for use, the sterility of the containers 108, and of the material placed therein, can be better controlled. As depicted in the figure, the containers 108 and outer container 124 can be formed from a transparent material.

The inlet 116 may be interconnected to a cannula and/or a reservoir of fat and/or other material to be placed in some or all of the containers 108, for example by a length of flexible tubing. An outlet 132 can also be included in the lid 120. In accordance with embodiments of the present invention, the outlet 132 is interconnected to a vacuum source. The outlet 132 can therefore be used to introduce a vacuum at the inlet 116, that promotes the receipt of material through the inlet 116, and the deposit of that material in the containers 108, as described more fully elsewhere herein.

Figure 2:
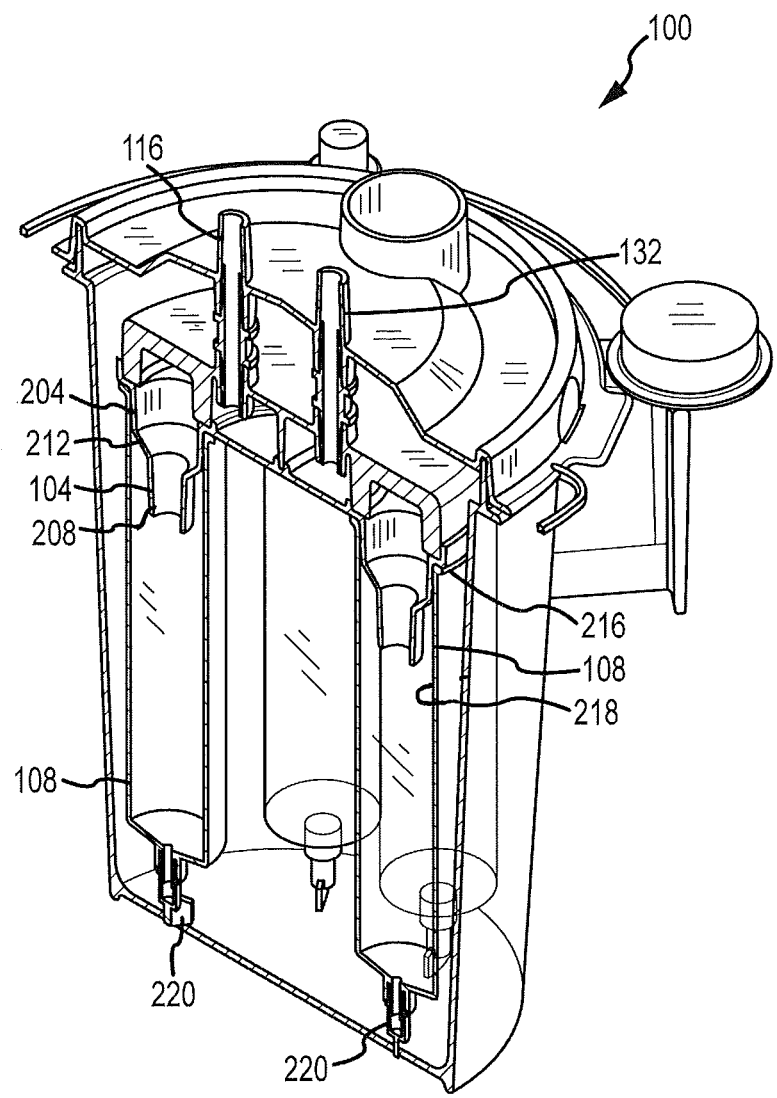
FIG. 2 is a cut away view of the system of FIG. 1.

FIG. 2 is a cut away view of the system 100 illustrated in FIG. 1. As can be seen in FIG. 2, each funnel 104 can feature a securement section 204 and a reduced section 208. Moreover, the securement section 204 can be interconnected or joined to the reduced section 208 by a transition section 212. In accordance with other embodiments of the present invention, the reduced section 208 can be joined directly to the securement section 204. In such or in other embodiments, the securement section 204 may be tapered. The containers 108 feature an open end 216 having an inner diameter that is equal to or about equal to the outer diameter of at least a portion of the securement section 204 of an associated funnel 104. Accordingly, a container 108 may be joined to an associated funnel 104 through a friction fit established between the inner diameter or inner surface 218 of the container 108 and at least a portion of the securement section 204 of the funnel 104. Therefore, containers 108 can be disconnected from an associated funnel 104 by removing the lid 120 and manifold assembly 112 from the outer container 124 such that the containers 108 are withdrawn from the outer container 124, and rocking or sliding each container 108 off of an associated funnel 104. As shown in the example of the figure, the containers 108 can comprise syringe bodies or barrels. The end of the syringe bodies through which material is typically ejected, for example through a needle or cannula, is plugged by a stopper 220, at least while material is being collected in the container 108. In accordance with still other embodiments, the containers 108 can comprise syringes with perforated body portions. As also shown, the manifold assembly may be formed from a bottom plate or structure 304 that is joined to a top plate or structure 404.

Figure 3:
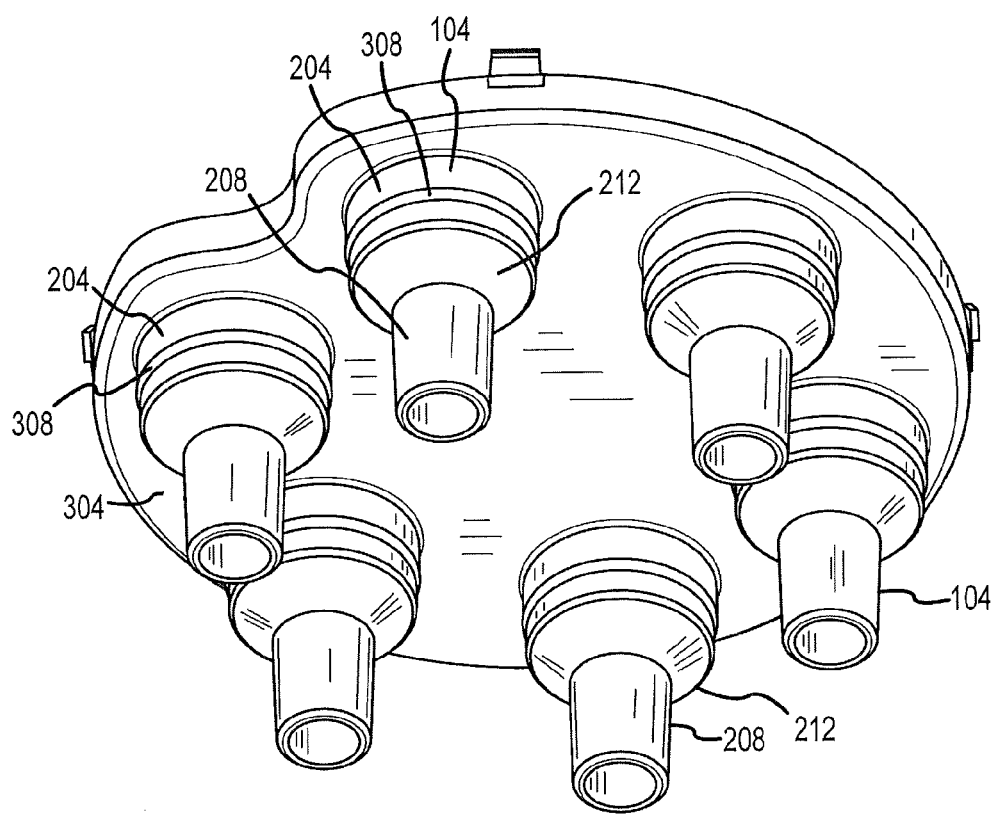
FIG. 3 is a bottom perspective view of a bottom plate of a manifold assembly in accordance with embodiments of the present invention.

FIG. 3 is a bottom perspective view of the bottom plate 304 of a manifold assembly 112 in accordance with embodiments of the present invention. In this embodiment, each funnel 104 includes a securement section 204, a reduced or tip section 208, and a transition section 212. In addition, each securement section 204 of each funnel 104 features an engagement surface 308. The engagement surface 308 can comprise an enlargement or bump that is integral to and that forms a ring type structure about the outer diameter of the securement section 204. In accordance with other embodiments, the engagement surface 308 can comprise an O-ring, band, or seal. Where the engagement surface 308 is separate from and is not integral to the securement section 204, the engagement surface 308 may be held within a groove or slot formed on the securement section 204.

Figure 4:
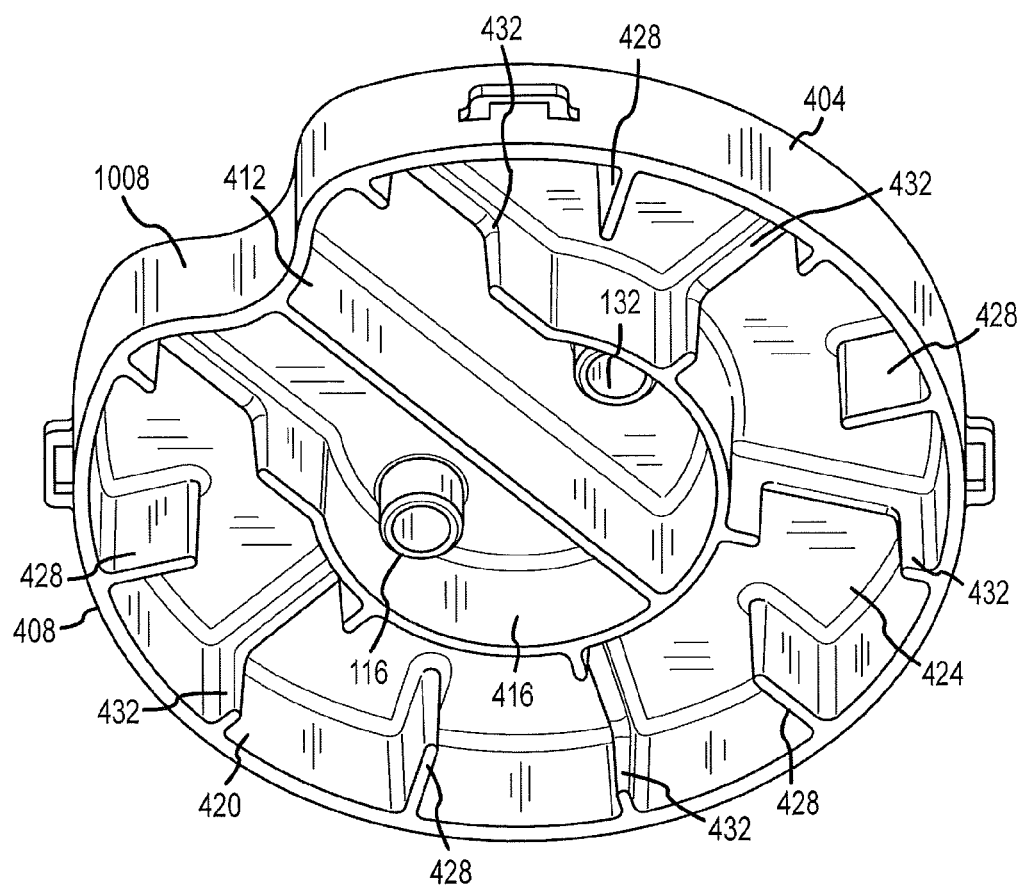
FIG. 4 is a bottom perspective view of a top plate of a manifold assembly in accordance with embodiments of the present invention.

FIG. 4 is a bottom perspective view of a top plate 404 of a manifold assembly 112 in accordance with embodiments of the present invention. More particularly, this view of the top plate 404 shows the material transfer channel 408 of the manifold assembly 112 in accordance with embodiments of the present invention. In particular, material is received through the inlet 116. Walls 412, 416 and 420 generally define the path of the material transfer channel 408, together with the top surface 424 of the top plate 404, and the adjacent surface of the bottom plate 304 when the bottom plate 304 is joined to the top plate 404. In particular, as material is introduced to the material transfer channel 408 through the inlet 116, it travels from the first end of the material transfer channel 408 towards the outlet 132, and drops into unfilled or partially filled funnels 104 along the path of the material transfer channel 408. In addition, the top plate 404 includes transverse walls 428 and transverse apertures 432 at different points along the material transfer channel 408. In general, the transverse walls 428 and transverse apertures 432 act to control the flow of material through the material transfer channel 408. The inclusion of the transverse walls 428 and transverse apertures 432 are believed to slow the progression of material from the first end of the material transfer channel 408 adjacent the inlet 116 to or towards the second end of the tissue transfer channel 408 adjacent the outlet 132, particularly when the material comprises or substantially comprises a fluid, such as fat removed from a body as part of a fat or tissue transfer process. By controlling the velocity of the material through or along the material transfer channel 408, the filling of the containers 108 can be facilitated. As an alternative or in addition to walls 412, 416, 420, and 428 and transverse apertures 432, partial walls, fences, speed bumps or other features that have the effect of lengthening the path defined by the tissue transfer channel 408 and/or of impeding the flow and reducing the velocity of material received through the inlet 116 can be provided. Moreover, walls 412, 416 and 420 and 428 and/or other like features can be provided by or interconnected to the bottom plate 304, as an alternative or in addition to the top plate 404. In an assembled state, the bottom plate 304 and the top plate 404 of the manifold assembly 112 may be adhered to one another.

Figure 5:
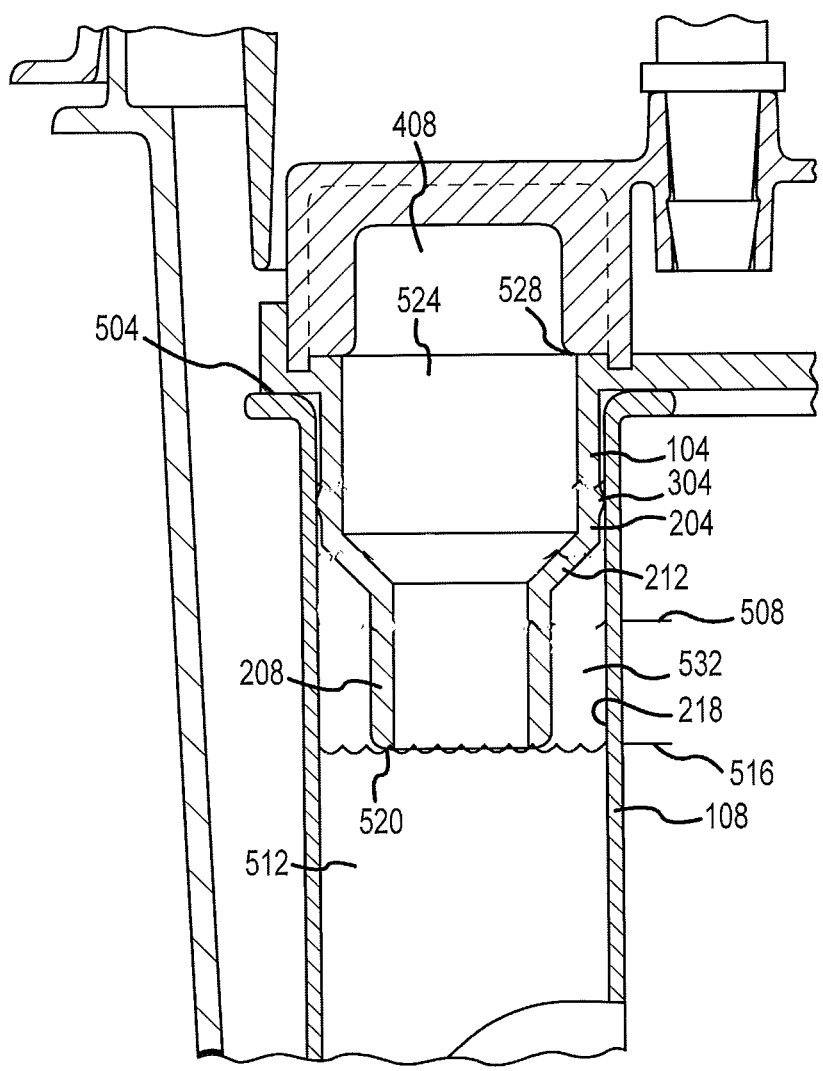
FIG. 5 is a partial cross-section of a funnel and attached container in a system in accordance with embodiments of the present invention.

With reference now to FIG. 5, a partial cross-section of a funnel 104 and container 108 in accordance with embodiments of the present invention is illustrated. The container 108 may have a maximum fill level that corresponds to the open end 504 of the container 108. However, the desired fill level is generally some distance from the open end 504 of the container 108. For example, where the container 108 comprises a syringe body or barrel, a syringe plunger would typically be placed through the open end 504 of the container 108, to force the material held by the container out the opposite end, e.g., through a needle into a body at an injection site. Therefore, in addition to helping to avoid spillage during transport or other handling of the container 108, providing a head space can help to avoid spillage during placement of the plunger in the container. The desired fill level 508 may correspond to a standard or commonly used volume of material, such as, for example and without limitation, 60 cc. Other examples of desired fill volumes for a container 108 include, without limitation, 1 cc, 5 cc, 10 cc, 30 cc, and 120 cc. As previously described, material is added to the container 108 via the funnel 104. As the volume of material within the container 108 increases, the material 512 eventually reaches an interim maximum fill level 516. As shown in connection with the exemplary embodiment of FIG. 5, the interim maximum fill level 516 can be at or about the bottom edge 520 of the funnel 104. The continued addition of material 512 results in the gradual filling of the funnel volume 524. When the material 512 reaches a level coincident with the top edge 528 of the funnel, any additional material 512 added to the system will pass to a next funnel 104 for placement in a container 108 associated with that next funnel 104 or if all of the containers 108 and funnels 104 are filled, will accumulate in the material transfer channel 408.

The annular volume 530 created between the fluid level 516 at or near the bottom 520 of the funnel 104 and the securement section 204 of the funnel 104 remains substantially free of material 512. The portion of the container 108 volume occupied by the funnel 104 and the annular volume 530 comprises a reserved volume 532. When the container 108 and the funnel 104 are disconnected from one another, the material 512 occupying the funnel volume 524 drops into the container 108. In accordance with embodiments of the present invention, the funnel volume 524 defined by the funnel 104 is selected to be less than the reserved volume 532 available in the container 108. Therefore, the level 508 of the material 512 in the container 108 when the funnel 104 is removed is somewhere between the level 516 corresponding to or near the bottom edge of the funnel 104 and the top edge 504 of the container 108. More particularly, embodiments of the present invention feature a funnel volume 524 that is selected to be equal to the volume between the fill level 516 in the container 108 when the funnel 104 is in place, and the desired fill level 508. Accordingly, a desired fill level 508 within a container 108 can be obtained simply by filling a container 108 and an associated funnel 104 until the material 512 reaches the top edge 528 of the funnel 104. Moreover, for a given container, different fill volumes can be obtained by providing funnels 104 that provide or create different funnel volumes 524 and different reserved volumes 532. In other embodiments, the interim maximum fill level 516 can correspond to a level that is noticeably above the bottom edge 520 of the funnel 104. In particular, as can be appreciated by one of skill in the art after consideration of the present disclosure, the interim maximum fill level 516 will depend on the areas of the various volumes, and the pressures on those volumes.

Figure 6A:
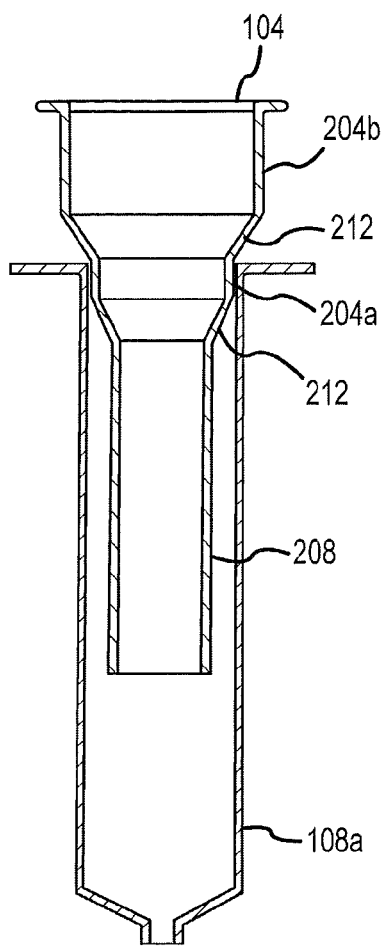
FIGS. 6A and 6B are partial cross-sections of a funnel and an attached container in accordance with other embodiments of the present invention.
Figure 6B:
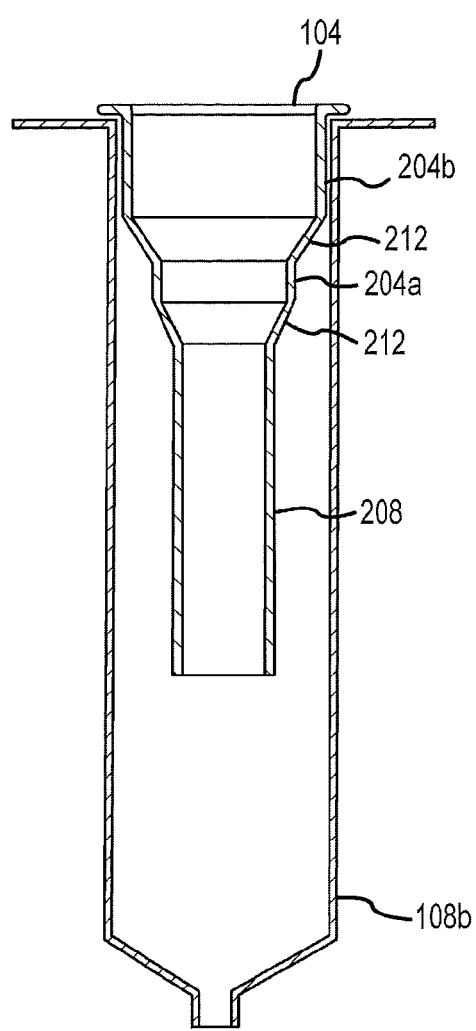

FIGS. 6A and 6B depict partial cross-sections of a funnel 104 and an interconnected container 108 in accordance with other embodiments of the present invention. In such embodiments, multiple securement surfaces 204 are provided by the funnel 104. In particular, moving from the top of the funnel 104, which is open to receive material from a material transfer channel 408, towards the end comprising the reduced section 208, each successive securement section 204 has a smaller diameter than the diameter of the previous securement section 204. This allows containers 108 different inside diameters to be accommodated by a funnel 104. For example, as shown in FIG. 6A, a container 108 comprising a 5 cc syringe can be connected to a first securement section 204a, and alternatively, as shown in FIG. 6B, a 10 cc syringe 108b can be connected to a second securement section 204b. Each securement section may be joined by a transition section 212. In accordance with still other embodiments, the securement section 204 may itself comprise a tapered or substantially conical section that can be secured to containers 108 of different diameters at different points along the length of the securement section 204.

Figure 7:
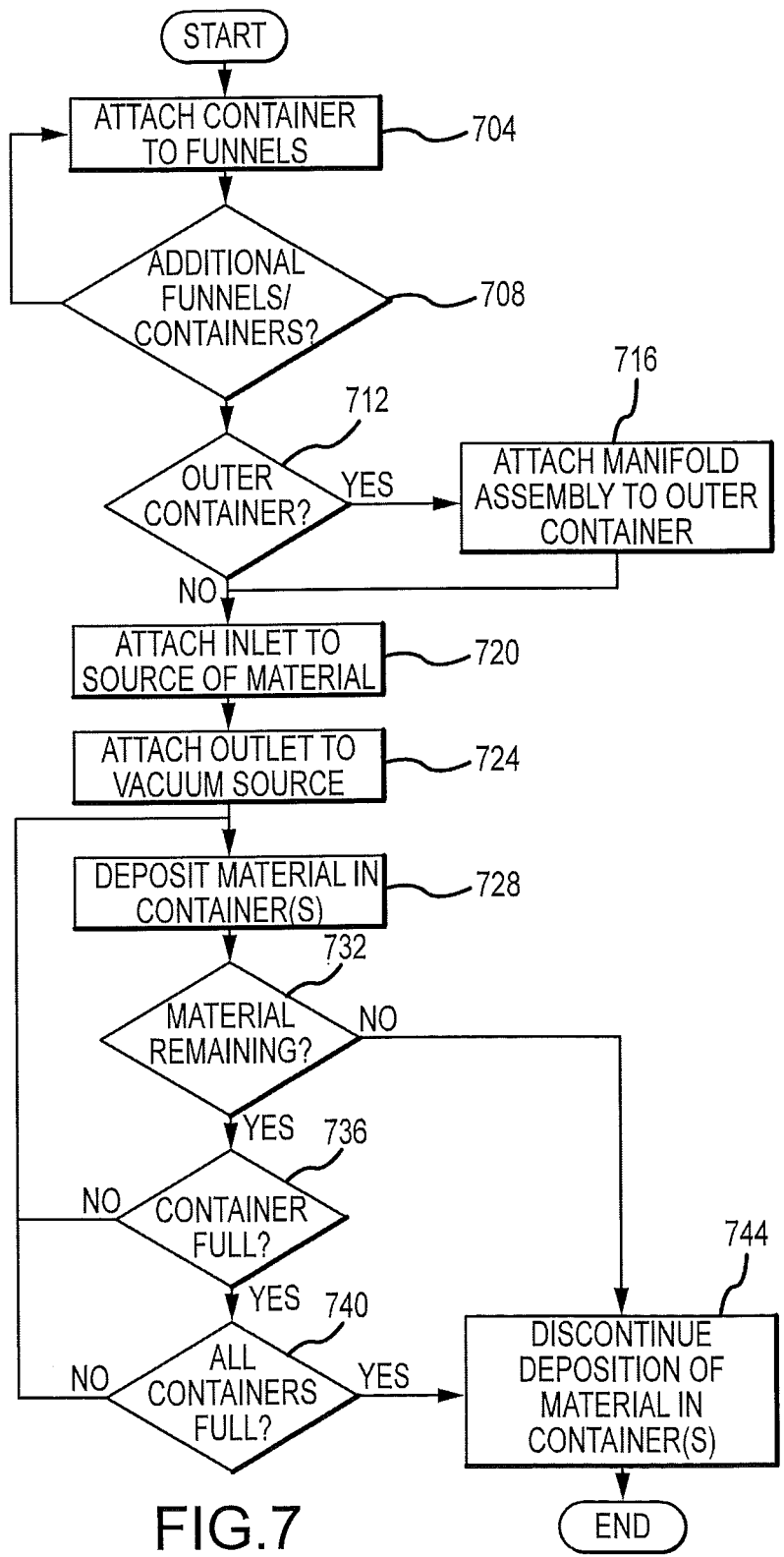
FIG. 7 is a flowchart depicting aspects of the operation of a system in accordance with embodiments of the present invention.

FIG. 7 is a flowchart illustrating aspects of the operation of a device or system for filling containers 108 in accordance with embodiments of the present invention. Initially, at step 704, a first container 108 is attached to a first funnel 104. At step 708, a determination is made as to whether there are additional funnels 104 and if so whether there are additional containers 108 for attachment to such funnels 104. If there are additional funnels 104 and containers 108, containers 108 can be attached to the additional funnels 104 until all of the funnels 104 are associated with a container 108. Alternatively, if there are no additional containers 108, but funnels 104 remain, the opening of the additional funnel or funnels 104 can be blocked. At step 712, a determination may be made as to whether the system 100 includes an outer container 124. If the system includes an outer container 124, the manifold assembly 112 can be attached to the outer container 124 (step 716). After attaching the manifold assembly 112 to the outer container 124, or if there is no outer container 124, the inlet 116 is attached to a source of material (step 720). For example, the source of material may comprise a fat deposit in a human body. Accordingly, attaching the inlet 116 to a source of material may, in accordance with embodiments of the present invention, comprise attaching the inlet 116 to a cannula via a length of flexible tubing. As another example, attaching the inlet 116 to a source of material can include attaching the inlet 116 to a reservoir containing fat or other material. At step 724, the outlet 132 is attached to a vacuum source, and the vacuum source can be operated to create a vacuum that can be used to draw material through the inlet 116.

At step 728, material drawn through the inlet 116 is deposited in the containers 108. In particular, material is drawn in through the inlet 116 by the vacuum introduced at the outlet 132. The material drawn into the inlet 116 is received at the first end of the material transfer channel 408, and drawn along the tissue transfer channel 408 to the first funnel 104. The material then drops into the funnel 104, and into the attached container 108. At step 732, a determination may be made as to whether material for placement in containers 108 remains. If material remains for placement in a container 108, a determination may next be made as to whether the container 108 is full (step 736). If the container 108 is not full, the process may return to step 728, and material may continue to be deposited in the container 108. If the container is full, a determination may be made as to whether all the containers 108 in the system 100 are full (step 740). If there are additional containers that are not full, the process may return to step 728, and material may be deposited in an additional container 108. In particular, in a multiple funnel 104 and container 108 system 100, when a first funnel 104 and container 108 are full, additional material received at the inlet 116 is drawn along the material transfer channel 408, past the first funnel 104 and container 108, to the next funnel 104 and container 108 that are available to receive additional material. If it is determined that any additional containers 108 are full, or if it determined that there is no additional material remaining for placement in containers 108, the deposition of material in containers 108 is discontinued (step 744). The process may then end.

Figure 8A:
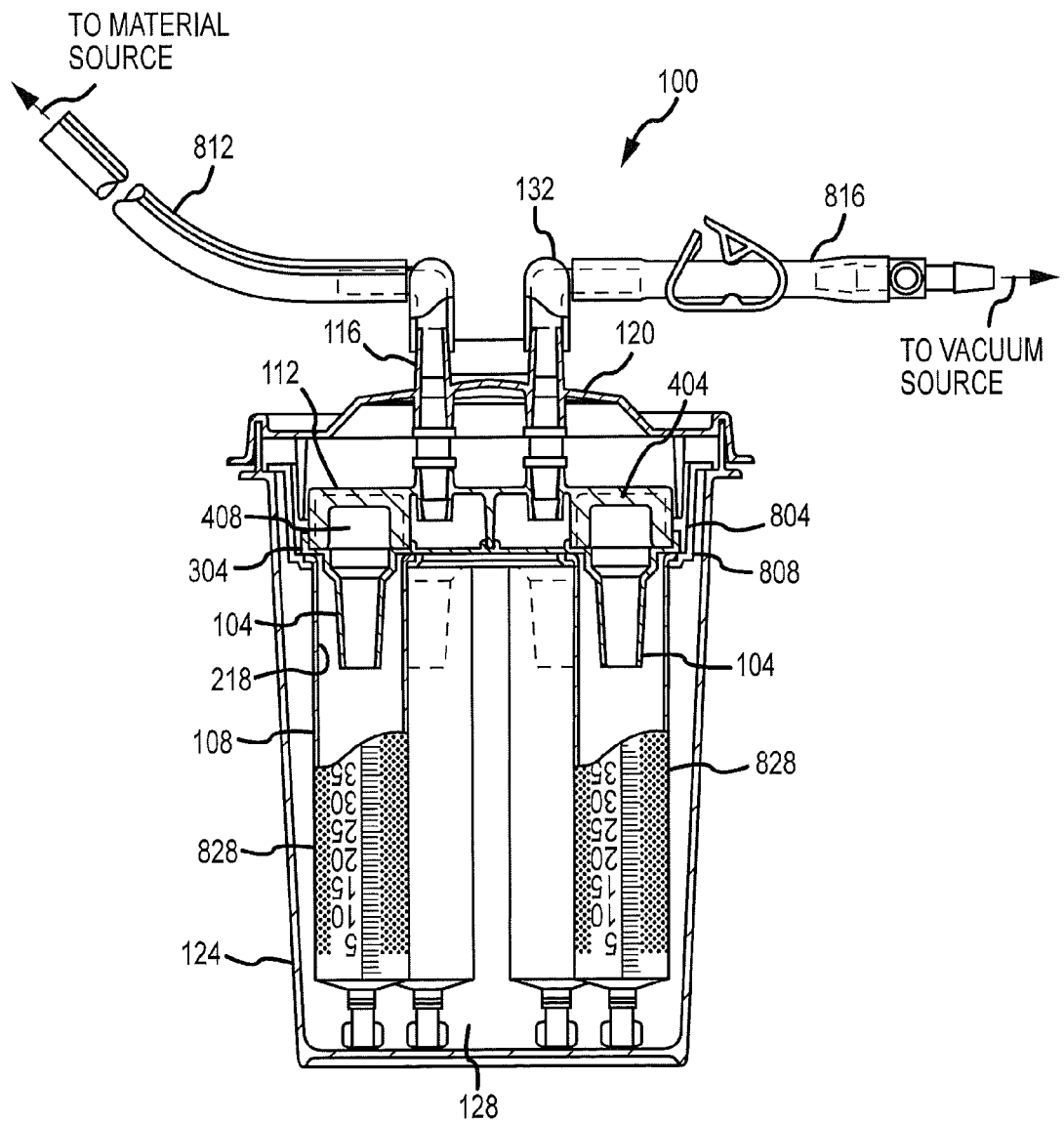
FIG. 8A is a front view in elevation of a system in accordance with embodiments of the present invention, with an outer container and a portion of a manifold and a container tray cut away.
Figure 8B:
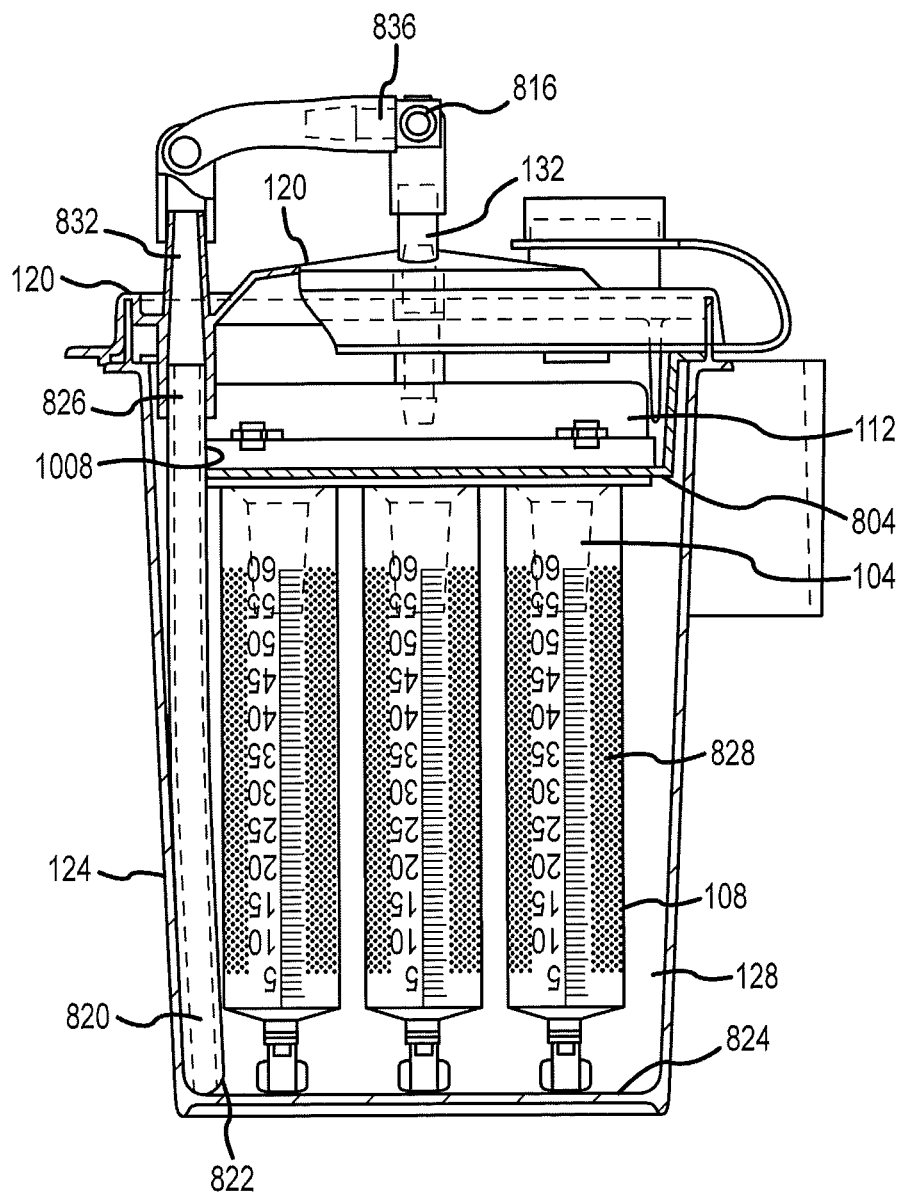
FIG. 8B is a side view in elevation of a system in accordance with embodiments of the present invention, with an outer container and portions of a manifold and a container tray cut away.

FIGS. 8A and 8B are cut away views in elevation of a system 100 for filling containers in accordance with further embodiments of the present invention. A difference between the embodiment illustrated in FIGS. 8A and 8B and some other embodiments described herein is that the funnels 104 are not in contact with the interior surface 218 of associated containers 108. Instead, the containers 108 are supported by a container tray 804 that is interconnected to the outer container 124.

Figure 9:
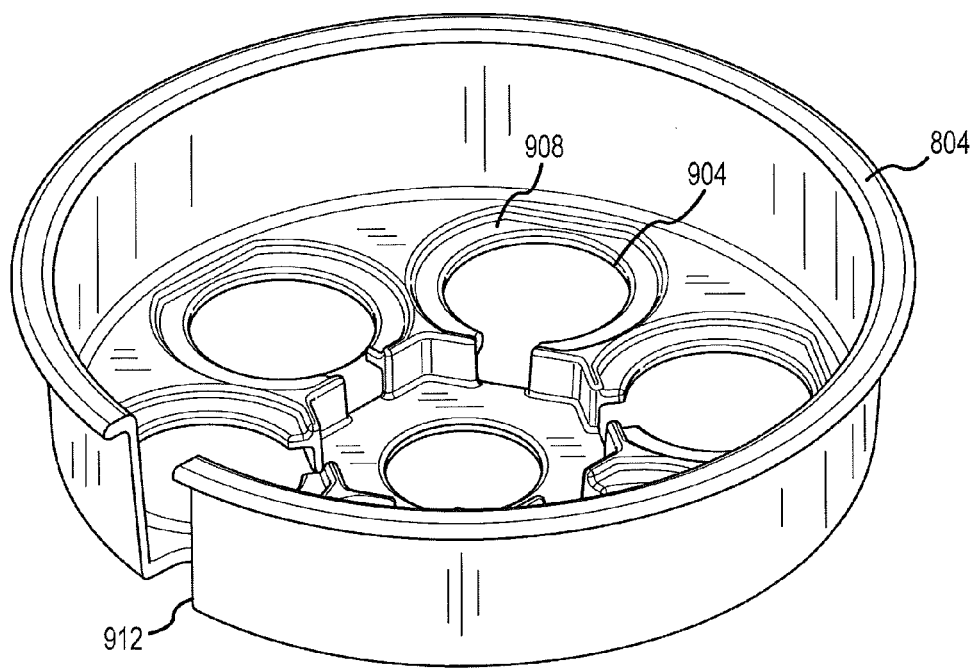
FIG. 9 is a top perspective view of a container tray in accordance with embodiments of the present invention.

With reference now to FIG. 9, a top perspective view of a container tray 804 in accordance with embodiments of the present invention is illustrated. As shown in the figure, the container tray 804 contains a plurality of apertures 904 sized to admit a body of a container 108 and associated recess 908 that are configured to receive an upper lip or flange 808 of a container 108. In particular, a container 108 can be dropped into each of the apertures 904 provided by the container tray 804. The container tray 804 can also include a clearance slot 912 to admit a waste tube as described elsewhere herein.

With reference again to FIGS. 8A and 8B, the funnels 104 are associated with a manifold assembly 112. The manifold assembly 112 receives material to be loaded into and/or filtered by the containers 108 through an inlet 116 formed in a lid 120. The lid 120 cooperates with the outer container 124 to define an enclosed volume 128 in which the containers 108 are located when the system 100 is assembled. The inlet 116 may be interconnected to a cannula and/or a reservoir of fat and/or other material to be placed in and/or filtered by the containers 108 by a length of flexible tubing 812. An outlet 132 can also be included in the lid and can be interconnected to a vacuum source by a second length of flexible tubing 816. Accordingly, a vacuum can be introduced at the outlet 132 that in turn creates a vacuum at the inlet 116, to promote the suction of material through the inlet 116. Moreover, some or all of the material received through the inlet 116 is deposited into the containers 108.

The manifold assembly 112 can include a top plate 404 and a bottom plate 304. The manifold 112 generally provides a material transfer channel 408 that extends between the inlet 116 and the outlet 132. Moreover, the funnels 104 of the system 100 establish or define a pathway between each container 108 included in the system 100 and the tissue transfer channel 408, when the system 100 is in an assembled state. Accordingly, material introduced to the tissue transfer channel 408 at the inlet 116 and drawn towards the outlet 132 by an applied vacuum can be deposited by gravity through the funnels 104 into associated containers 108. In addition, where multiple containers 108 are provided, those containers are filled progressively. Moreover, the inclusion of speed bumps, apertures, and walls (see FIG. 4), can create a circuitous path along the tissue transfer channel 408, which facilitates the progressive filling of the containers 108 by gravity. In addition, such features help prevent or avoid clogging of the outlet 120 with material drawn in through the inlet, by promoting the deposition of collected material in the containers 108, and by slowing the rate at which the material travels along the tissue transfer channel.

Figure 10:
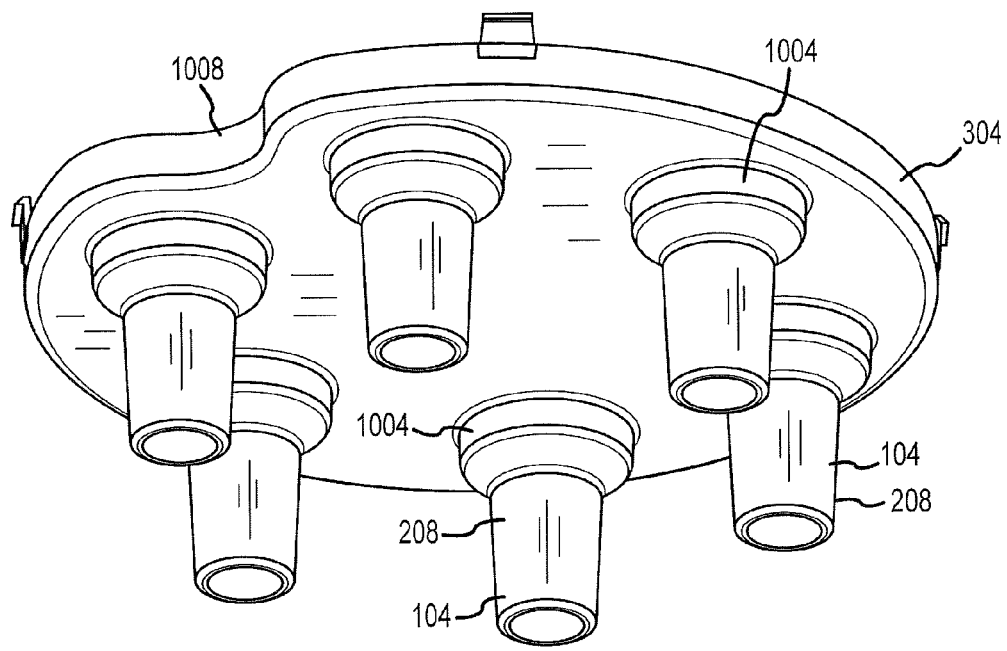
FIG. 10 is a bottom perspective view of a funnel plate in accordance with embodiments of the present invention.

With reference now to FIG. 10, a bottom perspective view of the bottom plate 304 of a manifold 112 in accordance with embodiments of the present invention is illustrated. As shown, a plurality of funnels 104 extend from a bottom planar portion of the bottom plate 304. In addition, the funnels 104 can include a straight or, as illustrated a tapered, tip section 208. Absent from the funnels 104 in such an embodiment is a securement section. Instead, the maximum diameter of each funnel 104, here corresponding to a base section 1004, has an outer diameter that is less than the inner diameter of an associated container 108. The bottom plate 304 also includes a clearance portion 1008, to allow a waste tube 820 to extend past the manifold assembly 112, to the bottom 824 of the outer container 124. The top plate 404 of the manifold assembly 112 for such embodiments can, but need not, be configured like the embodiment illustrated in FIG. 4, and like the top plate 404 can include a clearance portion 1008. In addition, the top plate 404 and/or the bottom plate 304 can include walls 412, 416, 420 and 428, transverse apertures 432, and/or other features to control the flow of material along the material transfer channel 408 (see FIG. 4). In an assembled state, the clearance portions 1008 of the bottom plate 304 and the top plate 404 are registered with the clearance slot 912 of the container tray 804, to provide a clearance space for the waste tube 820 (see FIG. 8B).

A system 100 as illustrated in FIGS. 8A and 8B can include containers 108 having perforations 828. As an example, and without limitation, the perforations can have a diameter of from 300μ to 1000μ. In accordance with still other embodiments, the perforations can have a hole size of 500μ, 600μ or 800μ. As can be appreciated by one of skill in the art after consideration of the present disclosure, a system 100 can be used to collect fat that can be re-injected into a body with little or no additional processing. In particular, fat and other fluids drawn in through the inlet 116 is deposited into containers 108. Where the containers 108 are perforated, fluids or small particles can pass through the perforations, and are collected in the outer container 124. That material can be collected from the bottom surface or floor 824 of the outer container 804 by the waste tube 820, which is open at a first end 822 lying on or adjacent the floor 824 of the outer container 124 and that is interconnected to a vacuum source at a second end 826, for example via a waste tube channel 832 in the lid 120 and a tee fitting 836 and associated tubing in communication with the outlet 132 and the vacuum source. In accordance with embodiments of the present invention, the first end 822 of the waste tube 820 can be shaped to maintain the end of the waste tube 820 in an open condition. For example, one or more teeth or serrations can be provided at the first end 822 of the waste tube 820.

Figure 11:
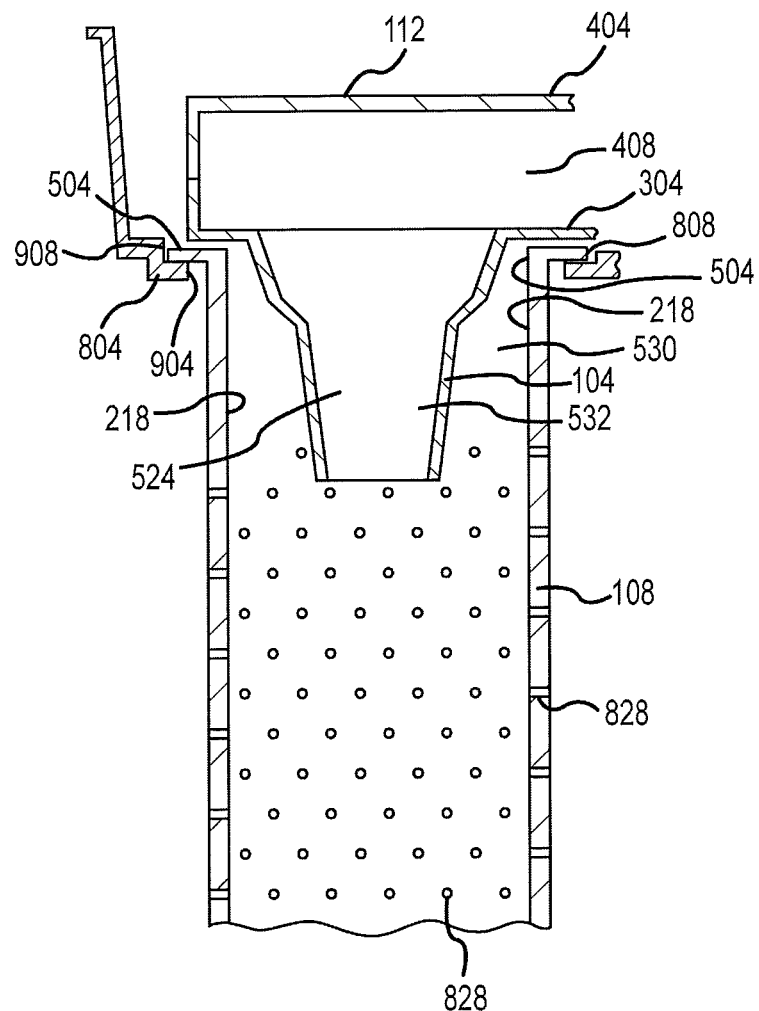
FIG. 11 is a partial cross-section in elevation of a funnel and container in accordance with other embodiments of the present invention.

FIG. 11 is a partial cross section of a funnel 104 and container 108 in accordance with embodiments of the present invention in which the funnel 104 is not in contact with the inner diameter or surface 218 of an associated container 108. In particular, the container 108 body has been inserted through an aperture 904 of the container tray 804, and is suspended in the container tray 804 by the upper lip or flange 808 of the container 108, adjacent the open end 504 of the container 108. In addition, the flange 808 of the container can be seated in a recess 908 surrounding the aperture 904. The funnel 104 is formed as part of the manifold 112, and provides for communication between the tissue transfer channel 408 and the interior of the container 108. The funnel 104 does not contact the inside surface 218 of the container 108. However, the funnel 104 does extend into a portion of the volume of the container 108. As with other embodiments, at least some of the portion of the container 108 volume 524 occupied by the funnel 104 and at least some of the annular volume 530 created between the funnel 104 and the interior surface 218 of the container 108 comprises a reserved volume 532. When the funnel 104 is withdrawn from the container 108, the material occupying available portions of the container 108 volume and the funnel 104 drops into the container 108. Moreover, the volume 524 defined by the funnel 104 is selected to be less than the reserved volume 532 available in the container 108. Therefore, the level of the material in the container 108 when the funnel 104 is removed is somewhere between the level corresponding to the bottom edge of the funnel 104 when the funnel 104 is positioned in the container 108 and the top edge 504 of the container 108. With respect to embodiments in which the container 108 includes perforations 828, the material retained in the container 108 will generally comprise material having a particle size that is greater than the size of the individual perforations 528. For example, perforations with a diameter of from 300μ to 1000μ can be used to retain fat in the container 108, while allowing fluids to drain out of the container 108.

Figure 12:
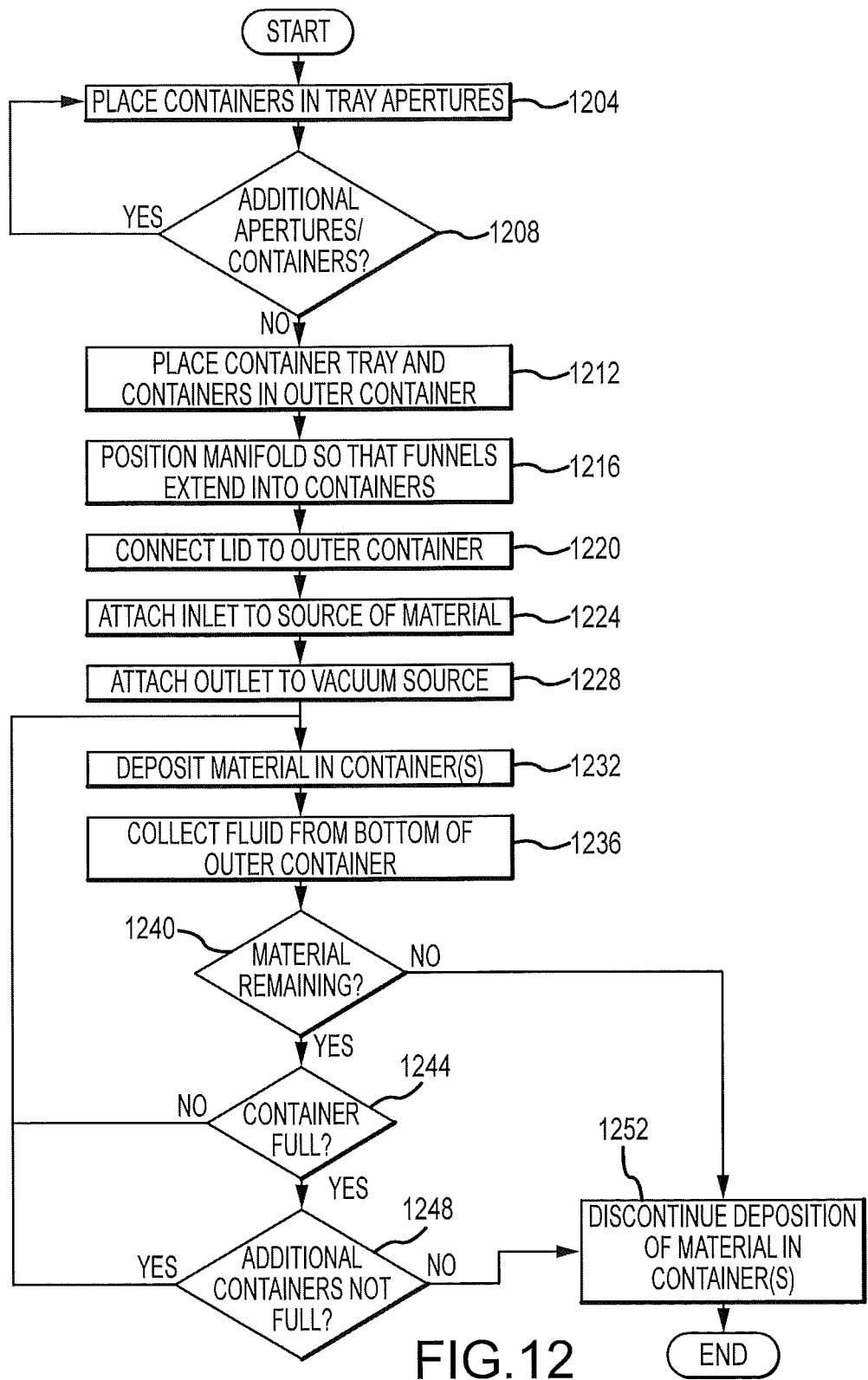
FIG. 12 is a flowchart depicting aspects of the operation of another system in accordance with embodiments of the present invention.

With reference now to FIG. 12, aspects of the operation of a system in accordance with further embodiments of the present invention, including embodiments with funnels 104 that do not contact an interior diameter 304 of associated containers 108, and with containers 108 that are perforated, are illustrated. Initially, at step 1204, the containers 108 are placed through the apertures 904 of the container tray 804. In accordance with embodiments of the present invention, this can include dropping a container 108 comprising a perforated syringe body into an aperture 904 of the container tray 804 until the flange 808 of the container 108 is held in the recess 908 provided by the aperture 904 of the container tray 804. At step 1208, a determination may be made as to whether there are additional apertures 904, and if so, whether there are additional containers 108 for placement in such apertures 904. If there are additional apertures 904 and containers 108, containers 108 can be placed in each of the apertures 904 until all of the apertures 904 have received and are associated with a container 108. At step 1212, the container tray 804 is placed in the outer container 124. Next, the manifold 112 is positioned such that the funnels 104 each extend into a container 108 (step 1216). Thus positioned, the bottom of the manifold 112 bottom plate 304 may be supported by the container tray 804. In addition, the manifold 112 is positioned such that the clearance slot 912 of the container tray 804 is registered with the clearance surface 1008 of the manifold 112. Thus configured, each funnel 104 at least partially extends into the interior volume of an associated container 108, but does not contact the interior surface 218 of the associated container 108. Next, at step 1220, the lid 120 is interconnected to the outer container 124. Interconnecting the lid 120 can include aligning the lid 120 such that an associated waste tube 820 extends through the space between the side wall of the outer container 124 and the manifold 112 at the clearance slot 912 and the clearance surface 1008. In accordance with embodiments of the present invention, by thus attaching the lid 120 to the outer container 124, the manifold 112, container tray 804, and containers 108 are held in an enclosed volume in communication with the inlet 116 and the outlet 132 via the funnels 104 and the material transfer channel 408.

At step 1224, the inlet 116 is attached to a source of material. As an example, the source of material may comprise a fat deposit in a human body. As another example, the source of material may comprise a reservoir containing fat or other material. At step 1228, the outlet 132 and the waste tube 820 are attached to a vacuum source, for example via a tee fitting 836, which is operated to create a vacuum that can be used to draw material through the inlet 116.

At step 1232, material drawn through the inlet 116 is deposited in the containers 108. In particular, the material is drawn in through the inlet 116 by the vacuum introduced at the outlet 132. Material drawn into the inlet 116 is received at the first end of the material transfer channel 408, adjacent the inlet 116, and is drawn along the tissue transfer channel 408 to the first funnel 104. The material then drops into the funnel 104 and from there into the associated container 108. If the container 108 includes perforations, fluids and particles that are smaller than the perforations can pass through those perforations 828 and are collected in the outer container 124. At step 1236, the fluid and other material collected in the outer container 124 is drawn from the floor 824 of that container 124 through the waste tube 820, under the influence of the vacuum applied by the vacuum source.

At step 1240, a determination may be made as to whether material remains for placement in the containers 108. If material remains for placement in a container 108, a determination may next be made as to whether the container 108 then being filled is full (step 1244). If the container is not full, the process may return to step 1232, and material may continue to be deposited in the container 108. If the container 108 is full, a determination may be made as to whether all of the containers 108 in the system 100 are full (step 1248). If there are additional containers that are not full, the process may return to step 1232, and material may be deposited in an additional or next container 108 in the series. In particular, in a multiple funnel 104 and container 108 system 100, when a first funnel 104 and container 108 are full, additional material received at the inlet 116 is drawn along the material transfer channel 408, past the first funnel 104 and container 108, to the next funnel 104 and container 108 that are available to receive additional material. If it is determined that all of the containers 108 are full, or if it is determined that there is no additional material remaining for placement in the containers 108, the deposition of material in containers 108 is discontinued (step 1252). The process may then end. Although various methods have been described and illustrated such that included steps are performed in a linear fashion, it should be appreciated that variations in the sequence of steps can be made in accordance with the present invention.

Although various examples given herein have discussed the deposition of material comprising fat in containers 108, it should be appreciated that embodiments of the present invention are not so limited. For example, embodiments of the present invention can be used to deposit any fluid, which may or may not contain suspended solids, in a container, up to a desired level in the container. In accordance with still other embodiments, material comprising gels or solids can be placed in one or more containers 108 up to a desired fill level. Moreover, although particular examples have discussed the use of containers 108 comprising syringe barrels, any container that can receive a funnel 104 can be filled with material using embodiments of the present invention. In addition, embodiments can include a single funnel 104 and container 108. In accordance with still other embodiments, a plurality of funnels 104 and containers 108 may be provided in a system that arranges the funnels 104 and the containers 108 in a linear fashion. Moreover, an outer container 124 is not required.

The dimensions of the funnel 104 are dependent on various factors. These factors include the dimensions of the container 108 that is to be filled, and the level to which the container 108 is to be filled. As an example, and without necessarily limiting the claims, in one embodiment the container 108 may comprise a syringe body with a nominal capacity of 60 cc. The inside diameter of the container 108 in this example is about 1.04 inches. As used herein, about means within about +/−10% of the stated value. Accordingly, the securement section 204 of the funnel 104 may have an outer diameter of about 1.0 inches, and an engagement surface 304 with an outer diameter that is slightly larger than the inner diameter of the container 108, to provide a friction fit between the funnel 104 and the container 108. Continuing this example, the securement section 204 of the funnel 104 may extend into the open end of the container 108 by about 0.5 inches, the securement section 204 may be joined to the reduced section 208 of the funnel 104 by a transition section 212 that has about a 45° taper that extends into the container 108 by about 0.25 inches, and the reduced section 208 may have an outer diameter of about 0.6 inches, and a length of about 0.6 inches. When the container 108 is filled to a level that is at or about the bottom edge of the reduced section 208 of the funnel 104, the container 108 is filled to a level that is less than the desired fill level by an amount that is about equal to the volume of the funnel 104. With respect to embodiments in which the container or containers 108 are perforated, a waste tube 820 can be provided to remove material passed through the perforations 828 of the containers 108 from the bottom surface 824 of the outer container 124. In addition, the perforations of such embodiments may have a hole size of from 300μ to 1000μ.

Figure 13:
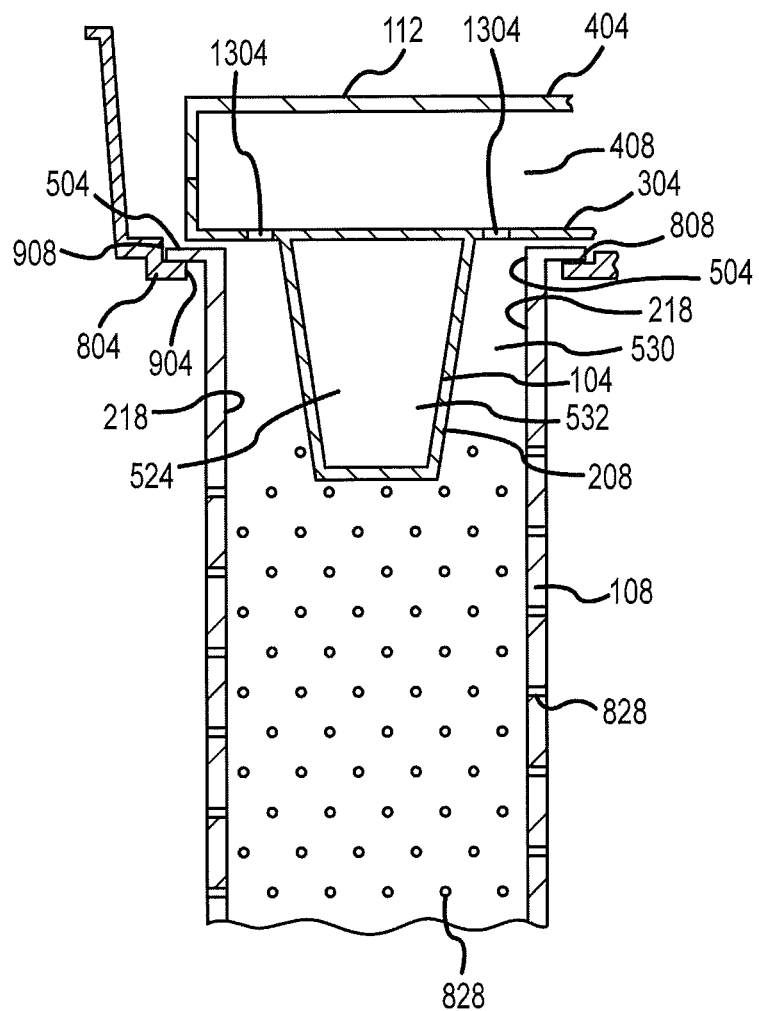
FIG. 13 is a partial cross-section in elevation of a solid funnel and container in accordance with embodiments of the present invention.

In accordance with further embodiments of the present invention, the volume 524 of a funnel 104 can be varied. In particular, by fixing an appendage to a funnel 104, such as a tip extension, the volume 524 of the funnel, and the reserved volume 532, can be altered. As shown in FIG. 13, in accordance with still other embodiments, material can be introduced to a container 108 via a pathway 1304 that extends between the material transfer channel 408 and the interior of the container 108, past an exterior of a funnel 104. Moreover, according to such embodiments, the funnel 104 can have a closed tip, or may comprise a solid or closed funnel structure or spacer. As shown in FIG. 13, the pathway 1304 can comprise one or more apertures in the floor of the bottom plate 304 of the manifold 112, that provide for communication between the material transfer channel 408 and the interior volume of the container 108 when a closed or inverted funnel 104 structure is used. In other embodiments of a configuration in which material passes around the exterior of the funnel or spacer, the funnel 104 can extend from the top plate 404 of the manifold assembly 112, a container 108 can be held within an aperture formed in the bottom plate 304, and an annular passage can be formed between the exterior surface of the funnel 104 and the open end 504 of the container 108.

Although specific examples of container fill volumes have been provided for purposes of illustration, embodiments of the present invention are not limited to specific amounts. Accordingly, by providing different funnel 104 dimensions and/or configurations, different fill volumes of an associated container 108 can be achieved. Exemplary fill volumes can extend from 60% to 95% of the maximum volume of a container 108. Other exemplary volumes extend from 75% to 80% of the maximum volume of a container 108.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. A system for filling one or more containers, comprising:
   a first funnel, the first funnel including an opening at a bottom edge thereof;
   a first container, including:
      a container volume;
      a first end, wherein the first end has an opening in communication with the container volume, wherein the first end and at least a portion of the container volume receive at least a portion of the first funnel including the opening at the bottom edge of the first funnel, wherein the opening at the bottom edge of the first funnel lies below the opening of the first end of the container, wherein the first funnel cooperates with the opening of the first end of the container to provide a sole communication path to the container volume, wherein the portion of the first funnel received by the container volume defines a reserved volume, and wherein except for the communication path provided by the opening at the bottom edge of the first funnel the container volume is a closed volume.

2. The system of claim 1, wherein the first funnel is not in contact with an interior surface of the first container.

3. The system of claim 1, wherein the first funnel further includes:
a securement section, wherein the securement section has a first outer diameter;
a reduced section, wherein the reduced section has a second outer diameter, wherein the first outer diameter is larger than the second outer diameter, and wherein the reduced section extends from the securement section;
an engagement surface, wherein the engagement surface engages the inner diameter of the first container.

4. The system of claim 3, wherein the engagement surface is integral to the securement section.

5. The system of claim 3, wherein the securement section of the first funnel includes a plurality of engagement surfaces, wherein each of the plurality of engagement surfaces has a different diameter, and wherein only one of the plurality of engagement surfaces engages the inner diameter of the first container.

6. A system for filling one or more containers, comprising:
a first funnel, the first funnel including an opening at a bottom edge thereof;
a first container, including:
a container volume;
a first end, wherein the first end has an opening in communication with the container volume, wherein the first end and at least a portion of the container volume receive at least a portion of the first funnel including the opening at the bottom edge of the first funnel, wherein the opening at the bottom edge of the first funnel lies below the opening of the first end of the container, wherein the first funnel cooperates with the opening of the first end of the container to provide a sole communication path to the container volume, and wherein the portion of the first funnel received by the container volume defines a reserved volume;
a material transfer channel, wherein the material transfer channel is in communication with the volume of the first container via the first funnel; and
a manifold assembly, wherein the material transfer channel is formed as part of the manifold assembly, and wherein the first funnel is interconnected to the manifold assembly.

7. The system of claim 6, further comprising:
a plurality of funnels, wherein at least the first funnel and a second funnel are included in the plurality of funnels, and wherein each funnel in the plurality of funnels defines a funnel volume that is in communication with the material transfer channel;
a plurality of containers, wherein at least the first container and a second container are included in the plurality of containers.

8. The system of claim 7, further comprising:
an outer container;
a lid, including:
an inlet port;
an outlet port, wherein the manifold assembly, the plurality of funnels, and the plurality of containers are held within a volume defined by the outer container and the lid, wherein the material transfer channel is in communication with the inlet port adjacent a first end of the material transfer channel, and wherein the material transfer channel is in communication with the outlet port adjacent a second end of the material transfer channel.

9. The system of claim 8, wherein the inlet port is interconnected to a cannula by a length of flexible tubing, and wherein the outlet port is interconnected to a vacuum source.

10. The system of claim 1, wherein the first funnel defines the volume and a first reserved volume, and wherein the reserved volume is greater than the first volume.

11. The system of claim 6, further comprising:
a plurality of at least one of transverse walls and transverse apertures disposed along the material transfer channel.

12. The system of claim 7, further comprising:
a plurality of at least one of transverse walls and transverse apertures disposed along the material transfer channel.

13. A system for filling one or more containers, comprising:
a first funnel;
a first container, including:
a container volume;
a first end, wherein the first end has an opening in communication with the container volume, wherein the first end and at least a portion of the container volume receive at least a portion of the first funnel, and wherein the portion of the first funnel received by the container volume defines a reserved volume;
a material transfer channel, wherein the material transfer channel is in communication with the container volume of the first container via the first funnel;
a manifold assembly, wherein the material transfer channel is formed as part of the manifold assembly, and wherein the first funnel is interconnected to the manifold assembly;
a plurality of funnels, wherein at least the first funnel and a second funnel are included in the plurality of funnels, and wherein each funnel in the plurality of funnels defines a funnel volume that is in communication with the material transfer channel;
a plurality of containers, wherein at least the first container and a second container are included in the plurality of containers;
an outer container;
a waste tube extending to a floor of the outer container, wherein the plurality of containers are perforated.

14. The system of claim 13, wherein none of the funnels are in contact with an interior surface of any of the perforated containers.

15. A system for filling one or more containers, comprising:
a first funnel, the first funnel including an opening at a bottom edge thereof:
a first container, including:
a container volume;
a first end wherein the first end has an opening in communication with the container volume, wherein the first end and at least a portion of the container volume receive at least a portion of the first funnel including the opening at the bottom edge of the first funnel, wherein the opening at the bottom edge of the first funnel lies below the opening of the first end of the container, wherein the first funnel cooperates with the opening of the first end of the container to provide a sole communication path to the container volume, and wherein the portion of the first funnel received by the container volume defines a reserved volume;

a material transfer channel, wherein the material transfer channel is in communication with the volume of the first container via the first funnel; and a plurality of at least one of transverse walls and transverse apertures disposed along the material transfer channel.

16. A system for filling one or more containers, comprising:

a first funnel;

a first container, including:

a container volume;

a first end, wherein the first end has an opening in communication with the container volume, wherein the first end and at least a portion of the container volume receive at least a portion of the first funnel, and wherein the portion of the first funnel received by the container volume defines a reserved volume;

a material transfer channel, wherein the material transfer channel is in communication with the volume of the first container via the first funnel;

a manifold assembly, wherein the material transfer channel is formed as part of the manifold assembly, and wherein the first funnel is interconnected to the manifold assembly;

a plurality of funnels, wherein at least the first funnel and a second funnel are included in the plurality of funnels, and wherein each funnel in the plurality of funnels defines a funnel volume that is in communication with the material transfer channel;

a plurality of containers, wherein at least the first container and a second container are included in the plurality of containers, wherein the first funnel and the second funnel are interconnected to the manifold assembly.

* * * * *